United States Patent [19]

Jaggy et al.

[11] Patent Number: 4,528,289
[45] Date of Patent: Jul. 9, 1985

[54] CORYNANTHEINE DERIVATES, PROCESSES FOR THEIR PREPARATION, AND THEIR USE

[75] Inventors: Hermann E. W. Jaggy, Bad Schönborn; Shyam S. Chatterjee; Bernard L. Gabard, both of Karlsruhe, all of Fed. Rep. of Germany

[73] Assignee: Dr. Willmar Schwabe GmbH & Co., Fed. Rep. of Germany

[21] Appl. No.: 461,949

[22] Filed: Jan. 28, 1983

[30] Foreign Application Priority Data

Feb. 12, 1982 [DE] Fed. Rep. of Germany ....... 3204960

[51] Int. Cl.³ .................... C07D 459/00; A61K 31/40
[52] U.S. Cl. ...................................... 514/285; 546/70
[58] Field of Search .................. 546/70; 424/258, 256

[56] References Cited

PUBLICATIONS van Tamelen et al., J. Am. Chem. Soc., vol. 81, 3805, (1959).
Weisbach et al., Tetrahedron Letters No. 39, pp. 3457–3463, (1965).
Szantay et al., Chemical Abstracts, vol. 75, 36430c, (1971).
Janot et al, Helv. Chim. Acta., vol. 34, (1951), pp. 1207–1210.
van Tamelen et al, J. Am. Chem. Soc., vol. 91, (1969), pp. 7359–7377.

Primary Examiner—Robert Gerstl
Assistant Examiner—William A. Teoli, Jr.
Attorney, Agent, or Firm—Toren, McGeady, Stanger, Goldberg & Kiel

[57] ABSTRACT

The present invention provides corynantheine derivatives of the general formula:

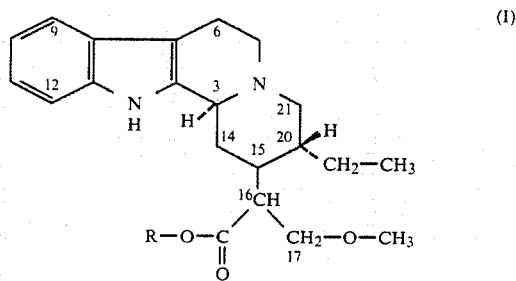

wherein R is a hydrogen or alkali metal atom, an ammonium group or the residue of an amine or an alkyl radical containing up to 4 carbon atoms; and the physiologically acceptable acid-addition salts thereof.

The present invention also provides processes for the preparation of these corynantheine derivatives and pharmaceutical compositions containing them. Furthermore, the present invention is concerned with the use of dihydrocorynantheine as an antihypertonic.

5 Claims, No Drawings

CORYNANTHEINE DERIVATES, PROCESSES FOR THEIR PREPARATION, AND THEIR USE

BACKGROUND OF THE INVENTION

1. Field of the Invention

The present invention is concerned with new derivatives of corynantheine and especially tetrahydrocorynantheine (THCN), as well as the pharmacologically acceptable acid-addition salts of these compounds, processes for the preparation thereof and pharmaceutical compositions containing these compounds, i.e. the use of the new corynantheine derivatives as medicaments.

2. Description of the Prior Art

A number of medicinal specialities are available commercially for the treatment of circulatory disturbances and for the therapy of high blood pressure. Nevertheless, there is still a number of cases of treatment in which the available preparations are ineffective or which are unsatisfactory because of their specific side effects or of their chronological course of action.

Thus, for example, raubasine (ajmalicine or δ-yohimbine) has been used as an active substance for decades in the therapy of circulatory disturbances. However, it has only a relatively short period of activity and, therefore, a continuous repetition of the administration thereof over short intervals of time is necessary.

Consequently, there is still a need for pharmacologically-active compounds and medicaments which possess a long-lasting blood pressure-lowering effectiveness but, at the same time, are as free as possible of unpleasant side effects.

SUMMARY OF THE INVENTION

It is an object of the present invention to satisfy the need for making available new pharmacologically-effective compounds and medicaments and especially of new antihypertonics and preferably those which, in the case of an equivalent dosing, bring about a stronger and longer-lasting blood pressure lowering and have a more favourable pharmacological profile than raubasine.

This object is achieved by making available the new compounds according to the present invention, by processes for the preparation of these compounds and by the use thereof as medicaments or as components of pharmaceutical compositions.

DESCRIPTION OF THE PREFERRED EMBODIMENTS

Thus, according to the present invention, there are provided corynantheine derivatives of the general formula:

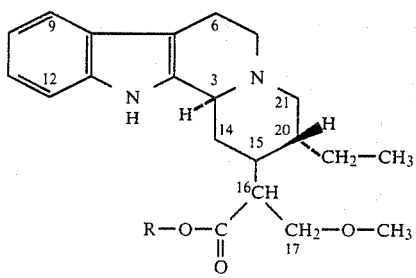

(I)

wherein R is a hydrogen or alkali metal atom, an ammonium group or the residue of an amine or an alkyl radical containing up to 4 carbon atoms, as well as the physiologically acceptable acid-addition salts thereof.

Besides an excellent blood pressure-lowering action, the compounds according to the present invention also possess an outstanding vasodilatory effectiveness and an activity influencing the central nervous system. The period of action of the compounds according to the present invention is significantly longer than that of the known compound raubasine. On the other hand, unpleasant side effects have hitherto not been ascertained in the case of the compounds according to the present invention.

The compounds according to the present invention can be prepared by partial synthesis, namely by the catalytic hydrogenation of the naturally-occurring compound corynantheine (Formula IIa) and of dihydrocorynantheine (Formula IIb), by the catalytic hydrogenation of mixtures of corynantheine and dihydrocorynantheine or of natural plant material containing these weakly basic indole alkaloids.

The indole alkaloids corynantheine (IIa) and dihydrocorynantheine (IIb), which occur naturally in the bark of *Pseudocinchona africana* A. Cheval (= *Corynanthe pachyceras*) and of *Corynanthe yohimbe* K. Schum., of the general formula:

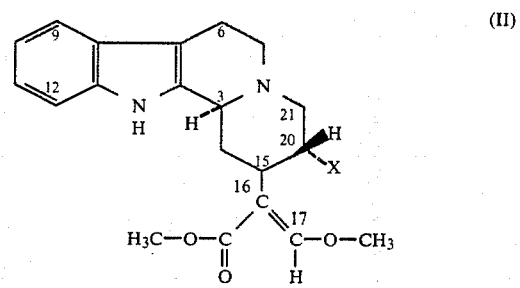

(II)

IIa: X=CH=CH$_2$

IIb: X=CH$_2$—CH$_3$ are known, naturally-occurring materials and are described as such in Helv. Chim. Acta, 9, 1059/1926 and in Helv. Chim. Acta, 35, 851/1952. The constitution of corynantheine is known from Helv. Chim. Acta, 34, 1207/1951 and the absolute configuration of dihydrocorynantheine and thus also that of corynantheine is known from Tetrahedron Letters, 39, 3457/1965. Also known is the catalytic hydrogenation of corynantheine and thus of its conversion into dihydrocorynantheine by means of palladium on barium sulphate (see Helv. Chim. Acta, 35, 851/1952) and by means of palladium on barium carbonate (see Compt. rend. hebd. Seance Acad. Sci., 234, 1562/1952).

On the other hand, a possible pharmacological effectiveness or a therapeutic possibility of use of the natural materials corynantheine and dihydrocorynantheine has hitherto not been disclosed. It has merely been mentioned that compositions of the bark of Pseudocinchona have been used in African folk medicine against coughs, leprosy and fever (see F. R. Irvine, "Woody Plants of Ghana", pub. Oxford University Press, 1961, page 665).

Regardless of whether, in the preparation of the compounds according to the present invention, the starting material used is pure corynantheine or pure dihydrocorynantheine or mixtures thereof or natural material containing these two indole alkaloids, possibly also containing corynantheidine, which has been obtained, for example, from *Pseudocinchona africana,* the catalytic hydrogenation proceeds in such a manner that the exo-positioned vinyl radical of corynantheine is first hydrogenated to give the corresponding exopositioned ethyl radical, (exo)-dihydrocorynantheine thereby being formed.

The dihydrocorynantheine formed as an intermediate product need not, according to the process of the present invention, be isolated and, upon continuation of the catalytic hydrogenation, is hydrogenated on the double bond between $C_{16}$ and $C_{17}$ so that the compound according to the present invention of general formula (I), in which R is a methyl radical, is formed, this compound here being called "tetrahydrocorynantheine" (THCN).

According to the process of the present invention, the catalytic hydrogenation is always carried out up to saturation, i.e. until no further hydrogen is taken up. When the starting material to be hydrogenated contains corynantheine, for the preparation of the tetrahydrocorynantheine according to the present invention, two equivalents of hydrogen are necessary but when the starting material only contains dihydrocorynantheine, only one equivalent of hydrogen is required for the preparation of THCN.

The hydrogenation is preferably carried out in an alcoholic or aqueous alcoholic solution of the starting materials corynantheine and/or dihydrocorynantheine, the lower alcohols being especially preferred as solvents.

According to the present invention, the catalysts used are noble metal catalysts (palladium, platinum or rhodium) or also other metal catalysts, in each case in finely divided form, on conventional inert organic or inorganic carrier materials, preferably palladium/charcoal or nickel catalysts, for example Raney nickel or nickel on kieselguhr.

The hydrogenation is preferably carried out at a pressure of from 50 to 110 bar and at a temperature of from 20° to 100° C.

The tetrahydrocorynantheine formed by the process according to the present invention from corynantheine and/or dihydrocorynantheine is not a mixture of the enantiomers possible on $C_{16}$ but is a uniform compound. This follows, on the one hand, from the $^{13}C$ NMR spectrum (cf. Example 1) and, on the other hand, from the fact that, under different reaction conditions, even in the case of a variation of the solvent and catalyst, the tetrahydrocorynantheine obtained always has the same optical rotation. A further indication of the presence of only one of the theoretically possible isomers is the fact that, in the case of thin layer chromatography in various eluent systems, only one spot is always obtained. An enantiomeric mixture, which is certainly a diastereomeric mixture, would have to be separated by thin layer chromatography, as is the case with the diastereomeric compounds corynantheine and dihydrocorynantheine.

Tetrahydrocorynantheine of general formula (I), in which R is a methyl radical, prepared by the above-described process, can be converted into other compounds of general formula (I) in the manner described hereinafter: It can be saponified by known methods to give the free acid (R=H) and possibly converted with inorganic bases or physiologically acceptable amines into its salts or it can also be transesterified by known methods, thus it can be converted into compounds of general formula (I) in which R is an ethyl, n-propyl, isopropyl, n-butyl, isobutyl or tert.-butyl radical. The last-mentioned alkyl esters can, however, also be prepared via the free acid by reaction thereof with an appropriate alkanol containing 2 to 4 carbon atoms.

The compounds according to the present invention are converted into their physiologically acceptable salts by mixing solutions thereof in appropriate solvents or directly mixing the reaction solutions remaining after separation of the catalyst with an inorganic acid, for example a hydrohalic acid, sulphuric acid, nitric acid, phosphoric acid or the like, or with a strong organic acid, for example oxalic acid or methane-sulphonic acid. Tetrahydrocorynantheine according to the present invention is astonishingly stable towards acids and other agents and, in particular, is substantially more stable than dihydrocorynantheine with its enol ether grouping.

The present invention also provides a pharmaceutical composition which, in addition to conventional carrier and additive substances, contains one or more of the compounds according to the present invention and/or the physiologically acceptable salts thereof. Conventional carrier materials include, for example, water, vegetable oils, polyethylene glycols, glycerol esters, gelatine, carbohydrates, such as lactose or starch, magnesium stearate and talc. Conventional additive substances include, for example, preserving, stabilising, lubricating and wetting agents, emulsifiers, physiologically acceptable salts, buffer substances and colouring, flavouring and aroma substances. The choice of the carrier and additive materials depends upon whether the compounds according to the present invention are to be administered enterally or parenterally.

The pharmaceutical compositions according to the present invention can be used as medicaments in human and veterinary medicine, especially as an antihypertonic. The compounds according to the present invention can also be administered in combination with other known blood pressure-lowering active materials, for example with saluretics, hydrazinophthalazines and beta-blockers. The dosage of dihydrocorynantheine and of tetrahydrocorynantheine or of one of its acid-addition salts is, in the case of oral administration, 5 to 20 mg., two or three times daily, whereas in the case of intravenous administration is 1 to 5 mg. of the corresponding free base or of an equivalent amount of one of its acid-addition salts two or three times daily.

Finally, the present invention is also concerned with the use of dihydrocorynantheine (DHCN) as an antihypertonic.

For the preparation of tablets each with an individual weight of 100 mg. and containing 10 mg. of THCN base or of an equivalent amount of an acid-addition salt thereof, there are required:

1. 10 g. tetrahydrocorynantheine or an equivalent amount of one of its acid-addition salts
2. 49 g. microcrystalline cellulose
3. 20 g. lactose
4. 20 g. maize starch
5. 0.5 g. colloidal silicic acid
6. 0.5 g magnesium stearate.

Substances 1 to 4 are dry mixed for 10 minutes, subsequently a mixture of substances 5 and 6 is added thereto, mixing is continued for a further 10 minutes and the powder thus obtained is pressed on a tabletting machine to give tablets with an individual weight of 100 mg.

In the following Examples, which are given for the purpose of illustrating the present invention, use is made of the following abbreviations:

m.p. = melting point (uncorrected) (in Examples 1 to 8 and 17 determined in small melting point tubes and in Examples 9 to 16 determined with a melting point microscope).

decomp. = decomposition subl. = sublimation $[\alpha]_D^{20}$ = optical rotation at 20° C., sodium D line.

After the optical rotation values there are given the concentrations of the measured solutions, in the case of which c=2 means, for example, a concentration of 2 g./100 ml. of solution; in each case, the solvent is stated separately.

All temperatures are given in degrees Celsius (°C.).

The following Examples 1 to 8 are concerned with the preparation of "tetrahydrocorynantheine" (THCN) according to the present invention, i.e. the compound of general formula (I), in which R is a methyl radical, using different starting materials and different catalysts. Examples 9 to 16 are concerned with the preparation of various acid-addition salts of THCN. Example 17 is concerned with the preparation of the compound according to the present invention of general formula (I), in which R is a hydrogen atom.

EXAMPLE 1

Hydrogenation of an alkaloid mixture 30 g. of the chloroform extract of the bark of *Pseudocinchona africana* are dissolved in 500 ml. ethyl acetate and shaken out twice with 250 ml. amounts of 1N hydrochloric acid. After rendering the hydrochloric acid solution alkaline with 25% ammonia solution to pH 8, the solution is shaken out three times with 250 ml. amounts of ethyl acetate. The combined ethyl acetate phases are washed with 300 ml. water, dried over anhydrous sodium sulphate and evaporated to dryness in a vacuum. The residue weighs 23 g. and contains 76.6% of alkaloids of the corynantheine type, consisting of 35.8% corynantheine, 28.6% corynantheidine, and 12.2% dihydrocorynantheine.

20 g. of the alkaloid mixture are dissolved in 100 ml. isopropanol/water (80/20 v/v). After the addition of 4 g. 10% palladium on active charcoal in 200 ml. isopropanol/water (80/20 v/v), the reaction mixture is hydrogenated in a high pressure autoclave at a hydrogen pressure of 70 bar, with shaking and external heating to 80° to 90° C., for 80 hours. (The reaction of corynantheine and dihydrocorynantheine to give tetrahydrocorynantheine can be monitored on silica gel: in the elution agent toluene/methylene chloride/isopropanol (75/20/5 v/v/v)+5 drops of 25% ammonia solution, there are obtained the following Rf values: corynantheine Rf=0.41, dihydrocorynantheine Rf=0.39, tetrahydrocorynantheine Rf=0.37 and corynantheidine Rf=0.60. After coloration with vanillin/phosphoric acid and heating on the thin layer chromatography plate for about 5 minutes to 120° C., the substance spots show the following colours:

corynantheine: deep blue-violet
dihydrocorynantheine: grey-violet
tetrahydrocorynantheine: deep blue violet
corynantheidine: pale violet-pink).

After completion of the hydrogenation, the catalyst is filtered off. The filtrate is evaporated in a vacuum to give 19.8 g. of residue. This is dissolved in 80 ml. 95% ethanol at the boiling point, the solution is filtered hot and, after cooling to ambient temperature, placed in a refrigerator. The crystals which precipitate out are filtered off with suction. Further substance crystallises out of the mother liquor. A total of 3.5 g. crystalline THCN are obtained.

The mother liquor from the second crystallisation (15.2 g.) can be fractionated over a column of 750 g. silica gel which has been rendered alkaline with 5% of its weight of a 25% ammonia solution, using the solvent system toluene/ethyl acetate (80/20 v/v). 2.3 g. of amorphous, crude THCN are obtained which, after recrystallisation from 95% ethanol, gives 1.2 g. of crystalline THCN.

The yield amounts to 48.5%, referred to the total amount of corynantheine and dihydrocorynantheine used; m.p. 215°–226° C. (the substance partially sublimes with decomposition above 175° C.); $[\alpha]_D^{20}$: −25° (c=2; chloroform); IR spectrum (KBr): 1720 (CO), 3365 cm$^{-1}$ (NH).

The $^{13}$C nuclear resonance spectrum in CDCl$_3$ solution taken at 22.63 MHz, shows for the individual carbon atoms the following chemical displacements (in ppm, referred to tetramethylsilane as internal standard):

C-2, 134.908
C-3, 60.145 or 59.174
C-5, 53.348
C-6, 21.954
C-7, 108.422
C-8, 127.680
C-9, 118.294
C-10, 121.530
C-11, 119.588
C-12, 111.012
C-13, 136.364
C-14, 31.771
C-15, 40.618 or 39.916
C-16, 45.742
C-17, 72.335
C-18, 10.896
C-19, 23.356
C-20, 40.618 or 39.916
C-21, 60.145 or 59.174
OCH$_3$, 60.684
COOCH$_3$, 51.730
COOCH$_3$, 173.261

For analysis, 0.5 g. of the recrystallised THCN is again recrystallised from 10 ml. 95% ethanol. Pure crystals are obtained with a melting point of 218°–219° C.

elementary analysis: C$_{22}$H$_{30}$N$_2$O$_3$ (M.W. 370.50), calc.: C 71.32%; H 8.16%; N 7.56%; O 12.96%, found: 71.37%; 8.39%; 7.34%; 12.90%.

EXAMPLE 2

Hydrogenation of a corynantheine/dihydrocorynantheine mixture with palladium/charcoal 10 g. of a crystalline corynantheine/dihydrocorynantheine mixture (about 27 mmol) are dissolved in 100 ml. n-propanol/water (80/20 v/v). After the addition of 1.5 g. 10% palladium on charcoal in 200 ml. n-propanol/water (80/20 v/v), hydrogenation is carried out at 60 bar hydrogen pressure, with shaking and at an external temperature of 90° C., for 82 hours (the thin layer chromatographic sample showed only a little non-hydrogenated dihydrocorynantheine). After filtering off the catalyst, the filtrate is evaporated to dryness in a vacuum, 9.74 g. of residue being obtained. Recrystallisation thereof from 50 ml. 95% ethanol gives 3.12 g. tetrahydrocorynantheine and from the mother liquor a further 0.30 g. and 0.28 g. thereof. Separation of the last mother liquor via silica gel gives a further 1.2 g. of crystalline THCN. The total yield of tetrahydrocorynantheine is 4.9 g., corresponding to 48.7% of theory. After recrystallisation from 40 ml. 95% ethanol, there are obtained 3.9 g. of white, needle-shaped crystals; m.p. 216°–218° C.; $[\alpha]_D^{20} = -24.5°$ (c=2; chloroform).

elementary analysis: $C_{22}H_{30}N_2O_3$ (M.W. 370.50), calc.: C 71.32%; H 8.16%; N 7.56%; O 12.96%, found: 71.79%; 8.46%; 7.42%; 12.33%.

EXAMPLE 3

Hydrogenation of dihydrocorynantheine with palladium/charcoal 10 g. of pure crystalline dihydrocorynantheine (27 mmol) are dissolved in 80 ml. 95% ethanol. After the addition of 2 g. 10% palladium on charcoal in 10 ml. 95% ethanol and subsequent rinsing with 10 ml. 95% ethanol, the autoclave is closed and flushed with nitrogen. Hydrogenation is carried out for 80 hours at a hydrogen pressure of 50 bar and at a temperature of 50° to 60° C. After cooling, crystals separate out from the hydrogenation mixture. By the addition of 100 ml. methanol, the crystals dissolve and the catalyst is filtered off from the solution. After evaporating the filtrate to dryness and crystallising the residue from 40 ml. 95% ethanol, there are obtained 7.4 g. of crystals of THCN. The yield is 19.97 mmol, corresponding to 73.97% of theory. For analysis, part of the substance is again recrystallised from 95% ethanol; m.p. 224°–226° C.; $[\alpha]_D^{20} = -25.5°$ (c=2; chloroform).

elementary analysis: $C_{22}H_{30}N_2O_3$ (M.W. 370.0), calc.: C 71.32%; H 8.16%; N 7.56%; O 12.96%, found: 71.76%; 8.45%; 7.47%; 12.32%.

EXAMPLES 4 TO 7

Hydrogenation of dihydrocorynantheine with various catalysts 3 g. amounts of dihydrocorynantheine are dissolved in 100 ml. isopropanol/water (80/20 v/v) or in n-propanol/water (90/10 v/v) and hydrogenated for 86 hours (Example 6: 2×86 hours) at 90° C. under a hydrogen pressure of 60 to 65 bar, whereafter, in each case, about half of the dihydrocorynantheine has been reacted to give THCN. After filtering off the catalyst, the filtrate is evaporated to dryness and the residue is recrystallised from 10 ml. 95% ethanol. The catalysts used and the melting points and the optical rotations of the resultant THCN are given in the following Table:

TABLE

| Example No. | 4 | 5 | 6 | 7 |
|---|---|---|---|---|
| catalyst | Pd/BaSO$_4$ | Pd/CaCO$_3$ | Pt/charcoal | Rh/charcoal |
| m.p. THCN | 222–226° C. | 222–225° C. | 218° C. | — |
| $[\alpha]_D^{20}$ | −27.75° c = 0.4 CHCl$_3$ | −27.25° c = 0.4 CHCl$_3$ | −25.5° c = 2 CHCl$_3$ | — |

EXAMPLE 8

Hydrogenation of an alkaloid mixture with nickel catalyst 140 g. of a toluene extract from the bark of *Pseudocinchona africana,* which has been subsequently purified as described in Example 1 by partitioning between hydrochloric acid and ethyl acetate, are dissolved in 1000 ml. isopropanol. After the addition of 30 g. nickel catalyst (55% by weight nickel on kieselguhr) in 200 ml. water and subsequent rinsing with 200 ml. isopropanol, hydrogenation is carried out in a high pressure autoclave equipped with a piston stirrer at 100 bar hydrogen pressure and at a temperature of about 90° C. for 120 hours. Thereafter, the catalyst is filtered off and the filtrate is evaporated to dryness on a rotary evaporator under water pump vacuum. After dissolving the residue in 500 ml. boiling 95% ethanol and clarification of the solution by filtration, the filtrate is cooled and placed in a refrigerator to give 26 g. of almost pure THCN. After again crystallising from 95% ethanol, the substance is chromatographically pure. Further THCN is obtained from the mother liquor after separating off accompanying materials via a silica gel column as described in Example 1 and recrystallisation from 95% ethanol.

EXAMPLE 9

Preparation of tetrahydrocorynantheine hydrochloride 13.3 g. pure crystalline tetrahydrocorynantheine are dissolved in 100 ml. analytically pure chloroform. While cooling the solution in an ice-bath, gaseous hydrogen chloride is passed in up to saturation, which can be recognised by the escape of hydrogen chloride vapours. The solution is then evaporated to dryness on a rotary evaporator under a vacuum at a bath temperature of 40° C., 18.31 g. of residue being obtained. This substance is taken up in 60 ml. analytically pure methanol and the solution clarified by filtering. While stirring, 180 ml. of a mixture of diethyl ether/petroleum ether (b.p. 40°–50° C.) (2/1 v/v) is added dropwise until the commencement of turbidity. For crystallising out, the mixture is placed in a refrigerator at −20° C. After filtering off the crystals with suction and drying at 110° C. for 8 hours under oil pump vacuum, there are obtained 12.4 g. of crystals. A further 1.17 g. of product crystallises out from the mother liquor. The combined first crystallisates are again recrystallised from methanol, with the addition of diethyl ether/petroleum ether. After drying, there are obtained 10.7 g. of product; m.p. 179°–183° C. (decomp. from 150° C., subl. of the base); $[\alpha]_D^{20} = 25.8°$ (c=2 in methanol).

For analysis, the product is again recrystallised from methanol by the addition of diethyl ether. After drying the crystals at 110° C. for 8 hours at oil pump vacuum, there are obtained slightly hygroscopic crystals; m.p. 187° C. (decomp. from 158° C., subl. of the base); $[\alpha]_D^{20} = -26°$ (c=2 in methanol).

elementary analysis: $C_{22}H_{30}N_2O_3 \times HCl$ (M.W. 406.96) calc.: C 64.93%; H 7.68%; N 6.88%; Cl 8.71%; O 11.79%, found: 64.60%; 7.88%; 6.79%; 8.90%; 11.83%.

EXAMPLE 10

Preparation of tetrahydrocorynantheine hydrobromide 0.65 g. (50 mmol) 47% hydrobromic acid is diluted with 20 ml. 95% pure ethanol and 1.85 g. (50 mmol)

THCN added thereto. The THCN thereby goes into solution at ambient temperature. (In a refrigerator, the salt precipitates out gelatinously). The solution is evaporated to dryness at 50° C. on a rotary evaporator. The residue is dissolved in 20 ml. analytically pure methanol and, while cooling with ice, a mixture of diethyl ether/petroleum ether (b.p 60°–70° C.) (2/1 v/v) is added dropwise until crystallisation commences. The precipitated salt is filtered off with suction and dried at 120° C. in a drying capsule to give 1.23 g. of crystals; m.p. 240°–242° C. (above 230° C. decomp.); $[\alpha]_D^{20} = -25.5°$ (c=0.2 in methanol). A further 0.38 g. of crystalline substance is obtained from the mother liquor. Yield 71.3% of theory.

elementary analysis: $C_{22}H_{30}N_2O_3 \times HBr$ (M.W. 451.42), calc.: C 58.53%; H 6.92%; N 6.20%; O 10.63%; Br 17.70%, found: 58.56%; 7.15%; 6.07%; 10.32%; 17.90%.

EXAMPLE 11

Preparation of tetrahydrocorynantheine nitrate 0.48 g. (50 mmol) 65% nitric acid is diluted with 20 ml. 95% pure ethanol and 1.85 g. (50 mmol) THCN added thereto. The THCN thereby goes into solution at ambient temperature. (No crystallisation occurs in the refrigerator). The solution is evaporated to dryness at 50° C. on a rotary evaporator. The residue is dissolved in 10 ml. analytically pure methanol, whereafter, while cooling with ice, diethyl ether is added thereto dropwise until crystallisation commences. The precipitated salt is filtered off with suction and dried at 120° C. in a drying capsule to give 1.66 g. crystals; m.p. 182° C. (from 175° C., subl. of the base); $[\alpha]_D^{20} = -31°$ (c=0.2 in methanol); yield 76.6% of theory.

elementary analysis: $C_{22}H_{30}N_2O_3 \times HNO_3$ (M.W. 433.52), calc.: C 60.95%, H 7.20%; N 9.69%; O 22.12%, found: 61.02%, 7.43%; 9.71%; 21.84%.

EXAMPLE 12

Preparation of tetrahydrocorynantheine hydrogen sulphate 0.49 g. (50 mmol) concentrated sulphuric acid are diluted with 20 ml. 95% pure ethanol, 1.85 g. (50 mmol) THCN is added thereto and the mixture heated on a waterbath until the THCN dissolves. The salt which crystallises out in a refrigerator is filtered off with suction and dried at 120° C. in a drying capsule to give 1.61 g. of crystals; m.p. 247°–248° C.; $[\alpha]_D^{20} = -25.5°$ (c=0.2 in methanol). A further 0.53 g. of crystalline substance is obtained from the mother liquor. Yield 91.3% of theory.

elementary analysis: $C_{22}H_{30}N_2O_3 \times H_2SO_4$ (M.W. 468.58), calc.: C 56.39%; H 6.88%; N 5.98%; O.23.90%; S 6.84%, found: 57.00%; 7.16%; 5.86%; 23.38%; 6.60%

EXAMPLE 13

Preparation of tetrahydrocorynantheine sulphate 0.245 g. (25 mmol) concentrated sulphuric acid is diluted with 20 ml. 95% pure ethanol and 1.85 g. (50 mmol) THCN added thereto. (The resultant milky turbidity is not clarified by boiling under reflux with 200 ml. ethanol). The solution is evaporated to dryness at 50° C. on a rotary evaporator. The residue is dissolved by boiling under reflux with 100 ml. analytically pure methanol and a part of the methanol is distilled off on a rotary evaporator. The salt which crystallises out upon standing in a refrigerator is filtered off with suction and dried at 120° C. in a drying capsule to give 1.66 g. of crystals; m.p. 244.5°–245.5° C.; $[\alpha]_D^{20} = -26°$ (c=0.2 in methanol). A further 0.25 g. of crystalline substance is obtained from the mother liquor. Yield 91% of theory.

elementary analysis: $C_{22}H_{30}N_2O_3 \times \frac{1}{2}H_2SO_4$ (M.W. 419.54), calc.: C 62.99%; H 7.45%; N 6.68%; O 19.07%; S 3.82%, found: 62.30%; 7.63%; 6.35%; 19.92%; 3.80%.

EXAMPLE 14

Preparation of tetrahydrocorynantheine methanesulphonate 0.48 g. (50 mmol) Methanesulphonic acid is dissolved in 20 ml. 95% pure ethanol and 1.85 g. (50 mmol) THCN added thereto. The THCN thereby goes into solution at ambient temperature. (No crystallisation takes place in a refrigerator). The solution is evaporated to dryness at 50° C. on a rotary evaporator. The residue is dissolved in 20 ml. ethanol. The salt which crystallises out in a refrigerator is filtered off with suction and dried at 120° C. in a drying capsule to give 1.28 g. of crystals; m.p. 243°–250° C. (from 175° C., subl. of the base); $[\alpha]_D^{20} = -27.50$ (c=0.2 in methanol). A further 0.38 g. of crystalline substance are obtained from the mother liquor. Yield 71.1% of theory.

elementary analysis: $C_{22}H_{30}N_2O_3 \times CH_3SO_3H$ (M.W. 466.62), calc.: C 59.20%; H 7.34%; N 6.00%; O 20.57%; S 6.87%, found: 59.42%; 7.61%; 5.82%; 20.15%; 7.00%

EXAMPLE 15

Preparation of tetrahydrocorynantheine dihydrogen phosphate 0.576 g. (50 mmol) 85% phosphoric acid is diluted with 20 ml. 95% pure ethanol and 1.85 g. (50 mmol) THCN added thereto. The THCN thereby goes into solution at ambient temperature (No crystallisation takes place in the refrigerator). The solution is evaporated to dryness at 50° C. on a rotary evaporator. The residue is dissolved in 10 ml. pure 95% ethanol, whereafter diethyl ether is added dropwise thereto until the commencement of crystallisation. The precipitated salt is filtered off with suction and dried at 120° C. in a drying capsule to give 1.94 g. crystals; m.p. 166°–167° C.; $[\alpha]_D^{20} = -24.5°$ (c=0.2 in methanol). Yield 76.9% of theory.

elementary analysis: $C_{22}H_{30}N_2O_3 \times H_3PO_4 \times 2H_2O$, (M.W. 504.52), calc.: C 52.38%; H 7.39%; N 5.55%; O 28.54%; P 6.14%, found: 52.15%; 7.08%; 5.36%; 29.51%; 5.90%.

EXAMPLE 16

Preparation of tetrahydrocorynantheine oxalate 0.315 g. (25 mmol) oxalic acid dihydrate is dissolved in 60 ml. analytically pure methanol. 1.85 g. (50 mmol) THCN is added thereto and the mixture is heated on a water-bath until the THCN dissolves and then filtered hot. The salt which crystallises out upon standing in a refrigerator is filtered off with suction and dried at 120° C. in a drying capsule to give 1.17 g. of crystals; m.p. 232°–233° C.; (above 158° C., subl. of the base); $[\alpha]_D^{20} = -27.81°$ (c=0.2 in methanol). A further 0.36 g. of crystalline substance is obtained from the mother liquor. Yield 72% of theory.

elementary analysis: $C_{22}H_{30}N_2O_3 \cdot \frac{1}{2}C_2H_2O_4 \times \frac{1}{2}H_2O$, (M.W. 424.53) calc: C 65.07%; H 7.60%; N 6.60%; O 20.73% found: 65.29%; 7.63%; 6.58%; 20.50%.

EXAMPLE 17

Preparation of tetrahydrocorynantheic acid 5 g. (13.5 mmol) Tetrahydrocorynantheine are heated under reflux for 6 hours with 500 ml. 2N hydrochloric acid. After cooling to ambient temperature, the pH is adjusted to about 9 by the portionwise addition of 2N aqueous sodium hydroxide solution, with external cooling. 0.14 g. Non-hydrolysed tetrahydrocorynantheine is removed by extracting twice with 200 ml. amounts of methylene chloride. The aqueous solution is acidified with glacial acetic acid to pH 6 to 6.5. After the addition of 20% ammonium sulphate, referred to the weight of the aqueous phase, extraction is carried out three times with 300 ml. amounts of methyl ethyl ketone. The combined organic phases are dried with anhydrous sodium sulphate and then evaporated to dryness on a rotary evaporator, 4.57 g. of residue being obtained. This is recrystallised from 250 ml. methyl ethyl ketone to give 3.83 g. of crystals. After recrystallising from 200 ml. methyl ethyl ketone and drying in a vacuum at 110° C., there are obtained 3.17 g. crystalline tetrahydrocorynantheic acid; m.p. 245°–248° C. (decomp.); $[\alpha]_D^{20} = -138°$ (c=0.2 in pyridine). Yield 64.2% of theory.

elementary analysis: $C_{21}H_{28}N_2O_3 \cdot \frac{1}{2}H_2O$ (M.W. 365.47) calc.: C 69.02%; H 8.00%; N 7.66%; O 15.32%, found: 68.92%; 8.09%; 7.43%; 15.56%

The free acid can be converted into its corresponding salts with inorganic bases, such as lithium hydroxide, sodium hydroxide, potassium hydroxide or aqueous ammonia solution, or with amines.

As already mentioned, the compounds according to the present invention possess an excellent blood pressure-lowering action, as well as outstanding vasodilatory and central nervous system-influencing properties. They are, therefore, preferably used as antihypertonics.

In the case of the pharmacological investigations described in the following, raubasine (=ajmalicine) was always used as the comparison compound.

The blood pressure-lowering action of the compound THCN according to the present invention and of DHCN was investigated on spontaneously hypertonic rats after oral administration and compared with that of ajmalicine. The method thereby used for the measurement of the systolic blood pressure and of the heart rate on rats is described in Arzneimittel-Forschung, 18, 1285–1287/1968. Before commencement of the experiments, the animals were familiarised with the measurement procedure.

In a first series of experiments, the systolic blood pressure and the heart rate were investigated 2 hours after the oral administration of the test substances in the form of their hydrochlorides. The substances were suspended in 0.2% agar and administered in a volume of 10 ml./kg. The results obtained are shown in the following Tables 1 to 3. It follows therefrom that all three substances lower the blood pressure in a dosage-dependent manner.

The calculation of the regression lines gives, in all three cases, a statistically significant correlation between dosage and degree of blood pressure lowering (cf. the following Table 4). For ajmalicine, in the case of a dosage of 56 mg./kg., the lowering reached a maximum of about 18%, which could not be exceeded with dosages of up to 100 mg./kg. A comparison with DHCN showed that both dosage activity curves run parallel (p=0.30) and that the distance of the two lines with p=0.65 is not significantly different from 0. On the other hand, the dosage activity curve for THCN is steeper and the action is stronger in higher dosages.

The heart rate is little influenced by all three substances. Neither a tendency nor a dosage dependence is thereby to be recognised.

In a further series of experiments, the chronological course of the blood pressure lowering was investigated. For this purpose, spontaneously hypertonic rats were treated with 10 mg./kg. DHCN and with 5 or 10 mg./kg. THCN per os and in each case 6 or 12 animals of the treated group were measured at definite times after the treatment.

The results obtained are given in the following Tables 5 and 6. DHCN (10 mg./kg.) and THCN (5 mg./kg.) have the same action, the maximum of which is reached about 40 minutes after administration. Thereafter, the blood pressure again increases to the initial value. THCN (10 mg./kg.) has a stronger action. 20 Minutes after administration, a maximum lowering of 30% is achieved. 6 Hours after administration, the blood pressure is still distinctly below the initial value.

The heart rate does not change after the administration of 5 mg./kg. THCN. After DHCN (10 mg./kg.) and THCN (10 mg./kg.), an increase is to be observed, which remains on the border of statistical significance.

The experiments show that especially THCN, in the case of oral administration, in comparison with ajmalicine, possesses a clearly stronger and longer-lasting blood pressure-lowering action.

In further experiments on different species, there was ascertained a lowering action of the compounds according to the present invention on the peripheral resistance, as well as vasodilatory effectiveness. The compounds according to the present invention display antagonistic and thus toxicity-inhibitory effectiveness against contractors, for example against noradrenaline, adrenaline and nicotine.

In further pharmacological investigations, it was ascertained that THCN possesses properties specifically influencing the central nervous system and antiarrythmic properties. Thus, after the oral administration of THCN, there was found a dosage-dependent (in the case of dosages of from 5 to 20 mg./kg.) sedating and body temperature-lowering action on mice. On the same animal and in the same dosage range, the compounds according to the present invention showed an inhibition of the "head twitch" syndrome caused by 5-hydroxytryptophane (experimental procedure according to Brit. J. Pharmacol., 20, 106–120/1963). It follows therefrom that THCN possesses a central antiserotoninergic action.

Furthermore, it was found that THCN, after oral administration to mice (in dosages of from 10 to 20 mg./kg.) potentiated the stereotypy brought about by apomorphine (for the method cf. Psychopharmacology, 50, 1/1976). This finding indicates a central dopaminergic-stimulating property of THCN. In contradistinction thereto, in this dosage range DHCN and ajmalicine display no properties influencing the central nervous system.

The antiarrhythmic effectiveness of DHCN and THCN was investigated on mice and rats. It was thereby found (cf. the following Table 7) that THCN, after interperitoneal administration, dosage-dependently inhibited the arrythmias caused by chloroform (for the method cf. J. Pharmacol. Exptl. Ther., 160, 22-31/1968). After intravenous administration (2 to 5 mg./kg.) to urethane-narcotised rats, THCN also protects against aconitine-induced arrythmias (for the method cf. Basic Res. Cardiol., 66, 73-79/1973). Ajmalicine, on the other hand, shows no antiarrythmic effectiveness in both models.

The toxicity of the compounds according to the present invention can be seen from the $LD_{50}$ values given in the following Table 8 for intravenous, intraperitoneal and oral administration. It can be seen therefrom that the toxicities of THCN, DHCN and ajmalicine are almost the same.

However, from the above-described pharmacological and toxicological investigations, it follows that the period and strength of activity of the compounds according to the present invention and of DHCN is greater than those of the known comparison compound ajmalicine. In addition, THCN possesses a favourable action specifically influencing the central nervous system and an antiarrhythmic action. On the basis of the indicated pharmacological activity profile, the compounds according to the present invention are suitable for the therapy of the following diseases:

1. central and/or peripheral circulatory disturbances
2. arrythmias
3. diseases of the central nervous system, the symptoms of which are to be attributed to a disturbance of the serotonin and/or dopamine metabolism
4. hypertonias
5. combinations of the above-mentioned diseases.

TABLE 1

Ajmalicine

| | | | systolic blood pressure in mm Hg | | | | heart rate beats/min. | | | |
|---|---|---|---|---|---|---|---|---|---|---|
| dosage | n | weight | previous value | subsequent value | Δ | Δ % | previous value | subsequent value | Δ | Δ % |
| 18 mg/kg | 3 | 211 ± 3 | 210 ± 6 | 198 ± 7 | −12 ± 2 | −5.6 ± 1 | 462 ± 42 | 492 ± 27 | 30 ± 15 | 7.3 ± 4.3 |
| 40 mg/kg | 6 | 202 ± 3.8 | 198 ± 6 | 173 ± 7 | −25 ± 6 | −12.4 ± 3 | 462 ± 17 | 513 ± 11 | 51 ± 19 | 11.9 ± 4.4 |
| 56 mg/kg | 5 | 213 ± 6 | 209 ± 8 | 172 ± 4 | −37 ± 5 | −17.5 ± 2.1 | 518 ± 6 | 522 ± 9 | 4 ± 9 | 0.8 ± 1.6 |
| 86 mg/kg | 5 | 218 ± 2 | 201 ± 6 | 165 ± 11 | −36 ± 12 | −17.7 ± 6.1 | 497 ± 9 | 511 ± 4 | 14 ± 2 | 2.9 ± 2.0 |
| 100 mg/kg | 5 | 218 ± 4 | 198 ± 6 | 165 ± 5 | −33 ± 9 | −16.3 ± 4 | 489 ± 5 | 515 ± 9 | 26 ± 11 | 5.3 ± 2.0 |

Systolic blood pressure and heart rate of spontaneously hypertonic rats before and 2 hours after administration of various dosages of ajmalicine hydrochloride (suspended in 0.2% agar, 10 ml./kg. per os).
Average values ± standard errors
n = number of animals.

TABLE 2

Dihydrocorynantheine

| | | | systolic blood pressure in mm Hg | | | | heart rate beats/min. | | | |
|---|---|---|---|---|---|---|---|---|---|---|
| dosage | n | weight | previous value | subsequent value | Δ | Δ % | previous value | subsequent value | Δ | Δ % |
| 4 mg/kg | 5 | 189 ± 3 | 199 ± 5 | 187 ± 6 | −12.7 ± 7 | −5.8 ± 3.3 | 479 ± 9 | 485 ± 14 | 6 ± 20 | 1.5 ± 4.2 |
| 8.6 mg/kg | 6 | 203 ± 5 | 200 ± 6 | 187 ± 5 | −13 ± 9 | −6.2 ± 4.0 | 472 ± 17 | 442 ± 19 | −30 ± 18 | −6.2 ± 3.7 |
| 18 mg/kg | 12 | 206 ± 3 | 202 ± 4 | 181 ± 3 | −21 ± 5 | −10.1 ± 2.1 | 496 ± 10 | 492 ± 12 | −4 ± 14 | −0.6 ± 2.9 |
| 32 mg/kg | 5 | 202 ± 4 | 204 ± 2 | 175 ± 10 | −29 ± 8 | −14.6 ± 4.1 | 493 ± 10 | 477 ± 5 | −16 ± 11 | −3.1 ± 2.2 |
| 56 mg/kg | 6 | 205 ± 4 | 193 ± 3 | 152 ± 6 | −41 ± 5 | −21.4 ± 2.7 | 491 ± 22 | 502 ± 14 | 3 ± 21 | 2.9 ± 3.8 |

Systolic blood pressure and heart rate of spontaneously hypertonic rats before and 2 hours after administration of various dosages of dihydrocorynantheine (suspended in 0.2% agar, 10 ml./kg. per os).
Average value ± standard errors.
n = number of animals.

TABLE 3

Tetrahydrocorynantheine

| | | | systolic blood pressure in mm Hg | | | | heart rate in beats/min. | | | |
|---|---|---|---|---|---|---|---|---|---|---|
| dosage | n | weight | previous value | subsequent value | Δ | Δ % | previous value | subsequent value | Δ | Δ % |
| 5 mg/kg | 12 | 205 ± 2 | 193 ± 6 | 178 ± 4 | −15 ± 3 | −7.7 ± 1.8 | 502 ± 12 | 508 ± 7 | 6 ± 12 | 1.2 ± 7.1 |
| 10 mg/kg | 12 | 213 ± 5 | 196 ± 3 | 168 ± 5 | −28 ± 6 | −14.3 ± 4.7 | 498 ± 6 | 519 ± 9 | 21 ± 11 | 4.2 ± 3.3 |
| 18 mg/kg | 6 | 208 ± 4 | 198 ± 7 | 165 ± 13 | −33 ± 11 | −16.5 ± 5.8 | 482 ± 17 | 495 ± 6 | 13 ± 12 | 3.3 ± 2.8 |
| 30 mg/kg | 6 | 204 ± 3 | 189 ± 8 | 146 ± 5 | −43 ± 5 | −21.9 ± 3.9 | 471 ± 20 | 493 ± 10 | 22 ± 27 | 4.7 ± 6.6 |
| 40 mg/kg | 6 | 203 ± 2 | 206 ± 4 | 132 ± 9 | −74 ± 10 | −35.7 ± 4.7 | 473 ± 22 | 472 ± 14 | −1 ± 29 | 1.0 ± 6.6 |

Systolic blood pressure and heart rate of spontaneously hypertonic rats before and after administration of various doses of tetrahydrocorynantheine (suspended in 0.2% agar, 10 ml./kg. per os)
Average value ± standard errors
n = number of animals

TABLE 4

| substance | correlation r | p | parameter of the line of regression slope | intercept |
|---|---|---|---|---|
| DHCN | 0.587 | <0.001 | 0.309 ± 0.075 | 4.31 ± 2.18 |
| THCN | 0.655 | <0.001 | 0.608 ± 0.115 | −7.99 ± 2.50 |
| Ajmalicine* | 0.660 | <0.01 | 0.312 ± 0.103 | −0.05 ± 4.45 |

Regression analysis of the dosage-activity relationship for ajmalicine, dihydrocorynantheine and tetrahydrocorynantheine
Values ± standard errors
*Only for the dosage 18 to 56 mg/kg.

TABLE 5

| substance (dosage) | initial value (100%) mm Hg | percentage decrease from time t = | | | | | | |
|---|---|---|---|---|---|---|---|---|
| | | 10 min. | 20 min. | 40 min. | 80 min. | 2 h. | 4 h. | 6 h. |
| DHCN 10 mg/kg | 180.6 ± 9.4 | 10.6*** ± 4.1 | 14.5*** ± 3.2 | 14.5*** ± 1.9 | 6.1** ± 2.8 | 3.7* ± 3.6 | 0.8 ± 4.2 | 1.4 ± 1.3 |
| THCN 5 mg/kg | 193.4 ± 7.3 | 11.1*** ± 2.0 | 13.8*** ± 2.0 | 12.8*** ± 3.1 | 13.8*** ± 2.2 | 8.1*** ± 2.2 | −0.2 ± 1.8 | 4.0* ± 2.0 |
| THCN 10 mg/kg | 196.7 ± 3.2 | 13.5*** ± 1.2 | 29.3*** ± 2.3 | 27.8*** ± 2.6 | 23.0*** ± 2.1 | 14.4*** ± 2.5 | 14.0*** ± 2.8 | 15.9*** ± 2.6 |
| ajmalicine 20 mg/kg | 188.6 ± 9.0 | 9.5*** ± 3.8 | 13.0*** ± 2.4 | 14.2*** ± 4.6 | 9.8*** ± 3.3 | 5.8** ± 2.4 | −1.2 ± 4.8 | −0.5 ± 1.4 |

Chronological course of blood pressure decrease after administration of dihydrocorynantheine and tetrahydrocorynantheine to spontaneously hypertonic rats.
average value ± standard errors number of animals see Table 6
*$p < 0.05$
**$p < 0.01$
***$p < 0.001$

TABLE 6

| substance (dosage) | n | initial value | heart rate at time t = | | | | | | |
|---|---|---|---|---|---|---|---|---|---|
| | | | 10 min | 20 min | 40 min | 80 min | 2 h | 4 h | 6 h |
| DHCN (10 mg/kg) | 6 | 479 ± 27 | 504 ± 15 | 515 ± 9 | 500 ± 8 | 516 ± 6 | 521 ± 3 | 517 ± 8 | 507 ± 9 |
| THCN (5 mg/kg) | 12 | 502 ± 12 | 504 ± 12 | 492 ± 7 | 499 ± 16 | 503 ± 10 | 508 ± 7 | 502 ± 9 | 489 ± 8 |
| THCN (10 mg/kg) | 12 | 499 ± 16 | 519* ± 7 | 518 ± 9 | 499 ± 12 | 520* ± 7 | 519* ± 6 | 519 ± 8 | 503 ± 8 |
| ajmalicine (20 mg/kg) | 6 | 492 ± 15 | 503 ± 12 | 505 ± 9 | 482 ± 9 | 481 ± 10 | 472 ± 10 | 499 ± 7 | 491 ± 17 |

Chronological course of heart rate of spontaneously hypertonic rats after administration of dihydrocorynanthiene and tetrahydro-corynantheine.
Average value ± standard errors
n = number of animals.
*$p \leq 0.05$

TABLE 7

| | Anti-arrhythmic action on mice | | |
|---|---|---|---|
| substance | dosage (mg/kg, i.p.) | n | inhibition in % of $CHCl_3$ arrhythmia |
| ajmalicine | 25 | 10 | 0 |
| DHCN | 25 | 10 | 80 |
| | 15 | 10 | 10 |
| | 10 | 10 | 0 |
| THCN | 25 | 10 | 90 |
| | 15 | 10 | 60 |
| | 10 | 10 | 10 | n = number of animals investigated.

TABLE 8

| $LD_{50}$ values (according to the method of Litchfield and Wilcoxon) on mice | | | |
|---|---|---|---|
| test substance | route of administration | $LD_{50}$ (mg/kg) | number of animals |
| THCN | i.v. | 14.1 (12.6–15.6) | 60 |
| | p.o. | 283.0 (267.0–300.0) | 50 |
| | i.p. | 133.3 (118.4–169.8) | 50 |
| DHCN | i.v. | 13.0 (11.2–15.0) | 50 |
| | p.o. | 210.0 (170.7–258.3) | 50 |
| | i.p. | 98.0 (83.0–115.7) | 50 |
| ajmalicine | i.v. | 14.0 (12.6–15.5) | 50 |
| | p.o. | 360.0 (315.5–410.4) | 50 |
| | i.p. | 90.0 (74.4–108.9) | 50 |

We claim:

1. Corynantheine compounds having the formula:

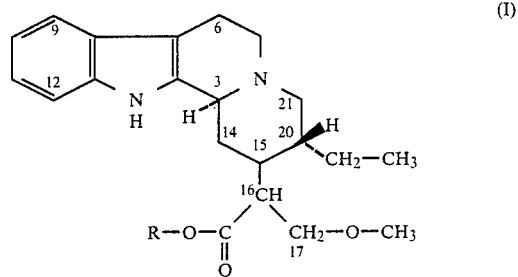

(I)

wherein R is a hydrogen or alkali metal atom, an ammonium group or an alkyl group having up to 4 carbon atoms; and the physiologically acceptable acid-addition or amine salts thereof.

2. Tetrahydrocorynantheine having the formula:

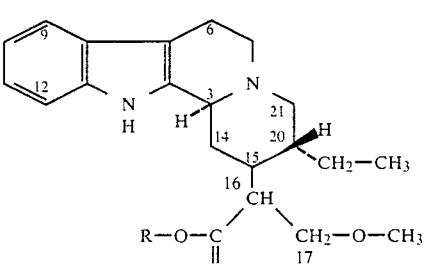

in which R is a methyl group, and the physiologically acceptable acid-addition salts thereof.

3. Tetrahydrocorynantheine acid having the formula:

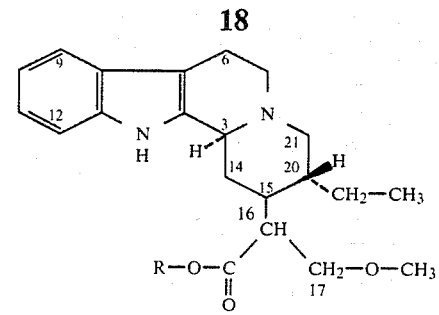

in which R is a hydrogen atom, and the physiologically acceptable salts thereof with inorganic bases and with physiologically acceptable amines.

4. A pharmaceutical composition containing an antihypertonic effective amount of at least one compound according to claim 1, 2, or 3 in admixture with conventional carriers and additives.

5. A method for lowering blood pressure comprising administering an antihypertonic effective amount of dihydrocorynantheine.

* * * * *